United States Patent [19]

Twinn

[11] Patent Number: 5,801,189
[45] Date of Patent: Sep. 1, 1998

[54] METHOD FOR COMBATING INSECTS

[75] Inventor: David Twinn, Essex, England

[73] Assignee: Rhone-Poulenc Agriculture Limited, Essex, United Kingdom

[21] Appl. No.: 658,252

[22] Filed: Jun. 4, 1996

Related U.S. Application Data

[63] Continuation-in-part of Ser. No. 425,205, Apr. 20, 1995, abandoned.

[30] Foreign Application Priority Data

Apr. 5, 1995 [GB] United Kingdom ............... 9507073

[51] Int. Cl.⁶ ............................ A01N 43/40; A01N 43/56
[52] U.S. Cl. ...................... 514/406; 514/336; 514/341; 514/404
[58] Field of Search ............................ 514/404, 406, 514/336, 341

[56] References Cited

U.S. PATENT DOCUMENTS

| | | | |
|---|---|---|---|
| 5,232,940 | 8/1993 | Hatton et al. | 514/407 |
| 5,236,938 | 8/1993 | Huang et al. | 514/341 |

FOREIGN PATENT DOCUMENTS

| | | |
|---|---|---|
| 0295117 | 12/1988 | European Pat. Off. . |
| 0385809 | 9/1990 | European Pat. Off. . |
| 0403300 | 12/1990 | European Pat. Off. . |
| 0679650 | 11/1995 | European Pat. Off. . |
| 19511269 | 10/1995 | Germany . |
| 87/03781 | 7/1987 | WIPO . |
| 93/06089 | 4/1993 | WIPO . |
| 94/21606 | 9/1994 | WIPO . |

*Primary Examiner*—Allen J. Robinson
*Attorney, Agent, or Firm*—Burns, Doane, Swecker & Mathis, L.L.P.

[57] ABSTRACT

Use of 1-phenyl pyrazole derivatives for surface treatment to control cockroaches or ants.

11 Claims, No Drawings

METHOD FOR COMBATING INSECTS

CROSS-REFERENCE TO RELATED APPLICATION

This is a continuation-in-part of prior U.S. patent application Ser. No. 08/425,205, filed Apr. 20, 1995, now abandoned, incorporated by reference herein in its entirety and relied upon.

This invention relates to a new method of combating insects such as cockroaches or ants at a locus connected to public health, that is to say at a locus frequented by humans, either private or public.

Many insecticidally active compounds are known, such as the insecticidal pyrazoles described in International Patent Publications No. WO 87/03781, WO 93/06089 and WO 94/21606, as well as in European Patent Publications 0295117, 0403300, 0385809, and 0679650, German Patent Publication 19511269 and U.S. Pat. Nos. 5,232,940 and 5,236,938. The use of such compounds to kill cockroaches or ants has already been contemplated, but such use was essentially in connection with baits or ingested materials or food that the insect is supposed to eat, or also in connection with direct contact application to the said insects.

The use of baits can be problematic because there is a need to place the baits at a proper locus where the cockroaches are supposed to come. Furthermore the baits can become a safety hazard to children, an undesirable situation.

An object of the instant invention is to provide a method of control of cockroaches or ants avoiding the use of baits or ingestible material.

An object of the instant invention is to provide a method of control of cockroaches or ants avoiding the direct application of the active material to the insect itself, as with baits for example.

The object of the instant invention is to provide a simplified and efficient method of control of cockroaches or ants.

The present invention is thus directed to a method of control of cockroaches or ants, preferably cockroaches, or of a population of cockroaches whereby an effective amount of an active ingredient which is a 1-phenylpyrazole derivative is applied to a surface on which the insect makes contact or moves or is moving or is expected to move.

The 1-phenylpyrazole derivatives which can be used in the invention are generally compounds of formula (I):

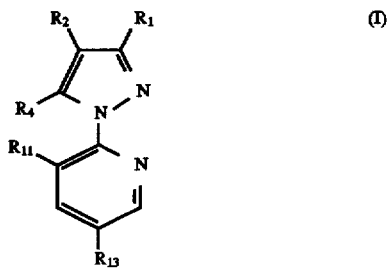

wherein:

$R_1$ may be CN or methyl;

$R_2$ may be $S(O)_n R_3$;

$R_3$ may be alkyl or haloalkyl;

$R_4$ represents a hydrogen or halogen atom; or a $NR_5R_6$, $S(O)_m R_7$, or $C(O)O-R_7$, alkyl, haloalkyl or $OR_8$ radical; or a $-N=C(R_9)(R_{10})$ radical;

$R_5$ and $R_6$, independently, may be a hydrogen atom or a radical alkyl, haloalkyl, C(O)alkyl or $S(O)_r CF_3$; or $R_5$ and $R_6$ may form together a divalent alkylene radical which may be interrupted by one or more divalent heteroatoms such as oxygen or sulfur;

$R_7$ may be an alkyl or haloalkyl radical;

$R_8$ may be an alkyl or haloalkyl radical, or a hydrogen atom;

$R_9$ may be a hydrogen atom or an alkyl radical;

$R_{10}$ may be a phenyl or heteroaryl group, optionally substituted by one or more halogen atoms or group such as OH, —O-alkyl, —S-alkyl, cyano, or alkyl;

$R_{11}$ and $R_{12}$, independently, represent a hydrogen or halogen atom;

$R_{13}$ represent a halogen atom or a haloalkyl, haloalkoxy, $S(O)_q CF_3$ or $SF_5$ group;

m, n, q, r may independently be an integer equal to 0, 1 or 2;

X represent a trivalent nitrogen atom or a C-$R_{12}$ radical, the three remaining free bonds of the carbon atom being part of the aromatic ring;

provided that, when $R_1$ is methyl, then $R_3$ is haloalkyl, $R_4$ is $NH_2$, $R_{11}$ is Cl, $R_{13}$ is $CF_3$, and X is N.

The alkyl and alkoxy radicals and alkyl and alkoxy portions of other radicals are preferably lower alkyl or lower alkoxy, that is to say, radicals having one to four carbon atoms.

When $R_5$ and $R_6$ together form alkylene optionally interrupted by one or two heteroatoms, —$NR_5R_6$ preferably represents a 3—to 8—membered ring.

When $R_{10}$ is heteroaryl, it is preferably pyridyl, most preferably 2-pyridyl.

A preferred class of compounds of formula (I) comprises the compounds of formula (I) wherein $R_1$ may be CN, and/or $R_3$ may be haloalkyl, and/or $R_4$ may be $NH_2$, and/or $R_{11}$, and $R_{12}$ are independently a halogen atom, and $R_{13}$ may be haloalkyl.

Still further preferred active ingredients which may be used in the invention are those of formula (I) wherein $R_{11}$ and $R_{12}$ are chlorine; $R_3$ and $R_{13}$ are trifluoromethyl; $R_5$ is amino.

Such most preferred insecticides are 5-amino-3-cyano-1-(2,6 dichloro-4-trifluoromethyl) phenyl-4-trifluoromethylsulfinylpyrazole (hereafter referred to as compound A), 5-amino-3-cyano-1-(2,6 dichloro-4-trifluoromethyl)phenyl-4-trifluoromethylthiopyrazole (hereafter referred to as compound B), 5-amino-3-cyano-1-(2,6 dichloro-4-trifltioromethyl) phenyl-4-trifluoromethylsulfonylpyrazole (hereafter referred to as compound C).

Compounds of formula (I) may be prepared according to known processes, for example as described in International Patent Publications No. WO 87/03781, 93/06089, and 94/21606 as well as in European Patent Publications No. 0295117, 0403300, 0385809 and 0679650, German Patent Publication No. 19511269 and U.S. Pat. Nos. 5,232,940 and 5,236,938 (all of which are incorporated by reference herein and relied upon in their entireties, especially for their description of compounds of formula (I) and methods for their preparation and use, both general and specific), or other process according to the knowledge of a man skilled in the art of chemical synthesis.

It should be understood that in the instant invention, the active ingredient is rather in the form of a thin layer or imbedded in a thin layer, and that this layer is covering totally or partially the surface where the insect is making contact or is moving or walking or going to walk or expected to be walking or supposed to be walking. Due to this thin layer the insect is not able to seize or bite or eat directly a discrete volume of composition comprising the ingredient of formula (I). This is connected with the unobviousness of the invention.

According to a further aspect of the invention, it provides a method of control of a population of cockroaches or ants able to walk or travel in public or private housing or building or household or home, whereby a non-seizable, but insecticidally effective, amount of active ingredient is lying on a surface located in the area to be treated.

According to a further aspect of the invention, it provides a method of control of a population of cockroaches or ants able to walk or travel in public or private housing or building or household or home, whereby a thin layer is covering the surface where the cockroaches or ants are supposed to walk.

According to a further aspect of the invention, it provides a method of control of a population of cockroaches or ants that are able to walk or travel in public or private housing or building or household or home, whereby said cockroaches or ants are caused to walk on a thin layer covering a surface in or near the area where the said insects are to be killed.

According to a preferred and most efficient embodiment, the invention is applied specifically to cockroaches.

The method of the invention is especially advantageous because it is very easy to apply the active ingredient, preferably by means of spraying a liquid formulation to the appropriate surface.

The surface which is treated according to the invention may be smooth or rough or rugged. Smooth surfaces are more effective. Various kinds of surface may be used such as glass, ceramics, concrete; plastics surfaces such as vinyl plastics, melamine, linoleum; metallic or wooden surfaces such as furniture; textiles such as clothes.

The deposited layer of active ingredient according to the invention may be wet just after application, or may be dried or dry sometime after. The creation of this layer may be made by all known methods of covering, for example as a spray coat, paint, dip, wash, soak, lacquer, foam, dust, powder, aqueous suspension, paste, cream, wettable powder, aerosol, emulsifiable concentrate, concentrated suspension, flowable suspension, aqueous suspension, oil suspension, oil solution, pressure pack, or other standard formulation well known by those skilled in the art.

Compositions comprising an active ingredient of formula (I), especially liquid compositions, have already been described in the hereinabove-cited prior art.

Treatment of cockroaches in public health in public housing or building for the control of so-called American cockroaches (*Periplaneta americana*), but also of other cockroaches like German cockroaches (*Blatella germanica*), is a preferred feature of the instant invention.

The invention accordingly provides a method for controlling cockroaches or ants which comprises applying to a surface with which the cockroaches or ants make contact or are to make contact a compound of formula (I). The compound is preferably applied as a thin layer.

The effective compositions which may be used in the invention may be offered or presented in different amounts. Usually, it is advantageous to offer the active compositions comprising the compound of formula (I) in an amount from about 0.0001 g to about 20 g per 100 square meters, preferably from about 0.01 g to about 10 g/100 m².

The compositions which are useful in the invention (and which are to be spread on surfaces to control cockroaches or ants) comprise generally from about 0.0001 up to about 15% w/w of active ingredient, preferably from about 0.1 to about 6% w/w. They may be in the form of a liquid before application, especially in the form of an emulsifiable concentrate, aqueous emulsion, concentrated suspension or flowable suspension. However, after drying of the liquid, the composition is in the form of a thin layer.

The insecticidal compositions may also contain any kind of compatible surface active agent and/or carrier. Adjuvants may also be used, such as sticking agents, dyestuffs, film-forming agents or the like. The carrier itself may be solid or liquid.

The compounds of formula (I) may be used in sequence or admixture, particularly admixtures with another pesticide e.g. an insecticide, acaricide or fungicide.

The compositions may be prepared by admixing the ingredients.

The invention is illustrated by the following examples which should not be considered as limiting or restricting the invention.

EXAMPLE 1

Compounds A and B were dissolved in an acetone/water mixture and deposited on glass and left overnight to dry. The following results were observed:

| COMPOUND | DOSE LEVEL mg/100 m² | Mortality % 90 min. after introduction of the cockroaches | Mortality % 18 h. after introduction of the cockroaches |
| --- | --- | --- | --- |
| B | 125 | 100 | 100 |
| B | 31 | 100 | 100 |
| B | 10 | 0 | 91 |
| A | 125 | 100 | 100 |
| A | 31 | 100 | 100 |
| A | 10 | 5 | 100 |

EXAMPLE 2

Compound A was formulated as a 12.5 grams per liter liquid formulation in three compositions: (i) an emulsifiable concentrate (EC-wetting agent and an organic solvent); (ii) an aqueous emulsion (EW-wetting agent plus water plus an organic solvent); and (iii) a concentrated suspension (SC-dispersing agent and water). Each formulation was dissolved in water and deposited on samples of painted cement and plastic flooring (as described in Methode C.E.B. n° 159 Chapitre II/§1, "Méthode d'essai d'efficacité practique de spécialités insecticides destinées a la destruction des blattes dans les locaux Novembre 1992," paragraph 2.6.) to provide deposits of 125 mg/100 m², 500 mg/100 m², and 1250 mg/100 m². *Blattella germanica* (German cockroaches) between 2 and 15 days old were placed on the surfaces for four hours and then removed, put in untreated jar and observed after 96 hours from the beginning of the exposure. Each treatment was replicated 3 times. The following results were observed. Mortalities are reported as percentages of dead insects among living ones.

| Formulation/Dose | Mortality % on Plastic | Mortality % on Cement |
| --- | --- | --- |
| EC/125 mg/100 m² | 10.2 | 100 |
| EC/500 mg/100 m² | 100 | 100 |
| EC/1250 mg/100 m² | 100 | 100 |
| EW/125 mg/100 m² | 93.3 | 100 |
| EW/500 mg/100 m² | 88 | 95.7 |
| EW/1250 mg/100 m² | 100 | 100 |
| SC/125 mg/100 m² | 93.3 | 100 |
| SC/500 mg/100 m² | 67.7 | 100 |
| SC/1250 mg/100 m² | 100 | 100 |

EXAMPLE 3

The samples of plastic flooring and cement of Example 2 were held at 25° C. in the dark for 24 hours. The infestation and observations of Example 2 were repeated. The following results were observed:

| Formulation/Dose | Mortality % on Plastic | Mortality % on Cement |
|---|---|---|
| EC/125 mg/100 m$^2$ | 14 | 100 |
| EC/500 mg/100 m$^2$ | 100 | 100 |
| EC/1250 mg/100 m$^2$ | 100 | 100 |
| EW/125 mg/100 m$^2$ | 49 | 100 |
| EW/500 mg/100 m$^2$ | 74 | 100 |
| EW/1250 mg/100 m$^2$ | 100 | 100 |
| SC/125 mg/100 m$^2$ | 43 | 100 |
| SC/500 mg/100 m$^2$ | 100 | 100 |
| SC/1250 mg/100 m$^2$ | 100 | 100 |

EXAMPLE 4

The samples of plastic flooring and cement of Example 2 were held at 25° C. in the dark for 14 days. The infestation and observations of Example 2 were repeated. The following results were observed:

| Formulation/Dose | Mortality % on Plastic | Mortality % on Cement |
|---|---|---|
| EC/125 mg/100 m$^2$ | 13.6 | 100 |
| EC/500 mg/100 m$^2$ | 100 | 100 |
| EC/1250 mg/100 m$^2$ | 100 | 100 |
| EW/125 mg/100 m$^2$ | 37.7 | 100 |
| EW/500 mg/100 m$^2$ | 77.7 | 100 |
| EW/1250 mg/100 m$^2$ | 100 | 100 |
| SC/125 mg/100 m$^2$ | 44.3 | 100 |
| SC/500 mg/100 m$^2$ | 100 | 100 |
| SC/1250 mg/100 m$^2$ | 100 | 100 |

EXAMPLE 5

The samples of plastic flooring and cement of Example 2 were held at 25° C. in the dark for 30 days. The infestation and observations of Example 2 were repeated. The following results were observed:

| Formulation/Dose | Mortality % on Plastic | Mortality % on Cement |
|---|---|---|
| EC/125 mg/100 m$^2$ | 6.7 | 72.3 |
| EC/500 mg/100 m$^2$ | 100 | 100 |
| EC/1250 mg/100 m$^2$ | 100 | 100 |
| EW/125 mg/100 m$^2$ | 53.3 | 100 |
| EW/500 mg/100 m$^2$ | 82.3 | 100 |
| EW/1250 mg/100 m$^2$ | 100 | 100 |
| SC/125 mg/100 m$^2$ | 51 | 100 |
| SC/500 mg/100 m$^2$ | 100 | 100 |
| SC/1250 mg/100 m$^2$ | 100 | 100 |

EXAMPLE 6

The samples of plastic flooring and cement of Example 2 were held at 25° C. in the dark for 90 days. The infestation and observations of Example 2 were repeated. The following results were observed:

| Formulation/Dose | Mortality % on Plastic | Mortality % on Cement |
|---|---|---|
| EC/125 mg/100 m$^2$ | 8.9 | 24.3 |
| EC/500 mg/100 m$^2$ | 95.7 | 100 |
| EC/1250 mg/100 m$^2$ | 100 | 100 |
| EW/125 mg/100 m$^2$ | 69 | 100 |
| EW/500 mg/100 m$^2$ | 95.7 | 100 |
| EW/1250 mg/100 m$^2$ | 100 | 100 |
| SC/125 mg/100 m$^2$ | 84.3 | 100 |
| SC/500 mg/100 m$^2$ | 100 | 100 |
| SC/1250 mg/100 m$^2$ | 100 | 100 |

EXAMPLE 7

The samples of plastic flooring and cement of Example 2 were held at 25° C. in the dark for 120 days. The infestation and observations of Example 2 were repeated. The following results were observed:

| Formulation/Dose | Mortality % on Plastic | Mortality % on Cement |
|---|---|---|
| EC/125 mg/100 m$^2$ | 4.3 | 8.8 |
| EC/500 mg/100 m$^2$ | 95.7 | 97.7 |
| EC/1250 mg/100 m$^2$ | 100 | 100 |
| EW/125 mg/100 m$^2$ | 69 | 100 |
| EW/500 mg/100 m$^2$ | 88.7 | 100 |
| EW/1250 mg/100 m$^2$ | 100 | 100 |
| SC/125 mg/100 m$^2$ | 86.7 | 100 |
| SC/500 mg/100 m$^2$ | 100 | 100 |
| SC/1250 mg/100 m$^2$ | 100 | 100 |

EXAMPLE 8

The samples of plastic flooring and cement of Example 2 were held at 25° C. in the dark for 180 days. The infestation and observations of Example 2 were repeated. The following results were observed:

| Formulation/Dose | Mortality % on Plastic | Mortality % on Cement |
|---|---|---|
| EC/125 mg/100 m$^2$ | 0 | 0 |
| EC/500 mg/100 m$^2$ | 100 | 100 |
| EC/1250 mg/100 m$^2$ | 100 | 100 |
| EW/125 mg/100 m$^2$ | 60 | 100 |
| EW/500 mg/100 m$^2$ | 93.3 | 100 |
| EW/1250 mg/100 m$^2$ | 100 | 100 |
| SC/125 mg/100 m$^2$ | 24.4 | 75.5 |
| SC/500 mg/100 m$^2$ | 100 | 100 |
| SC/1250 mg/100 m$^2$ | 100 | 100 |

EXAMPLE 9

Porous concrete is impregnated with a 20 ppm solution acetone/water solution of Compound B and cockroaches (*Blattella germanica*) were permitted to walk on the surface. One day after treatment, the insects were observed. 50% of the insects had died.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for controlling cockroaches, said method comprising treating a surface over which said cockroaches will move with the compound 5-amino-3-cyano-1-(2,6-dichloro-4-trifluoromethyl) phenyl-4-trifluoromethylsulfinylpyrazole, said compound being applied so as to be in the form of a thin layer or imbedded in a thin layer in a non-seizable amount sufficient to be insecticidally effective against said cockroaches when they move over the treated surface, said compound being applied as an insecticidal composition, said compound being lethal to said cockroaches not less than about 4 hours after their contact with the treated surface.

2. A method according to claim 1 wherein said insecticidal composition is an emulsifiable concentrate, an aqueous emulsion, a suspension concentrate or a flowable suspension.

3. A method according to claim 1, wherein said amount is of from about 0.0001 g to about 20 g per 100 square meters.

4. A method according to claim 2, wherein said amount is of from about 0.0001 g to about 20 g per 100 square meters.

5. A method according to claim 3, wherein said amount is of from about 0.01 g to about 10 g per 100 square meters.

6. A method according to claim 4 wherein said amount is of from about 0.01 g to about 10 g per 100 square meters.

7. A method according to claim 5, wherein said amount is of from about 125 mg to about 1250 mg per 100 square meters.

8. A method according to claim 6, wherein said amount is of from about 125 mg to about 1250 mg per 100 square meters.

9. A method according to claim 7, wherein said composition is an emulsifiable concentrate.

10. A method according to claim 7, wherein said composition is an aqueous emulsion.

11. A method according to claim 7, wherein said composition is a concentrated suspension.

* * * * *

UNITED STATES PATENT AND TRADEMARK OFFICE
CERTIFICATE OF CORRECTION

PATENT NO.    : 5,801,189
DATED         : September 1, 1998
INVENTOR(S)   : David Twinn Page 1 of 1

It is certified that error appears in the above-identified patent and that said Letters Patent is hereby corrected as shown below:

Column 1,
Lines 47-57, correct to read

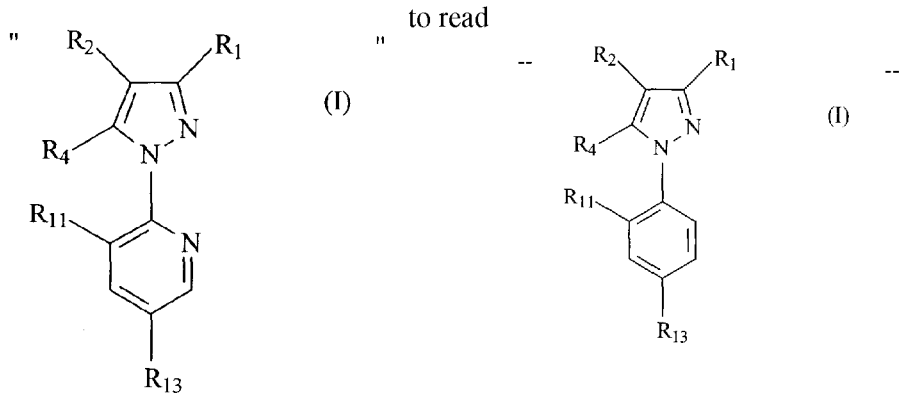

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 5,801,189
DATED         : September 1, 1998
INVENTOR(S)   : David Twinn Page 1 of 1

It is certified that error appears in the above-identified patent and that said Letters Patent is hereby corrected as shown below:

Column 1,
Lines 47-57, correct "  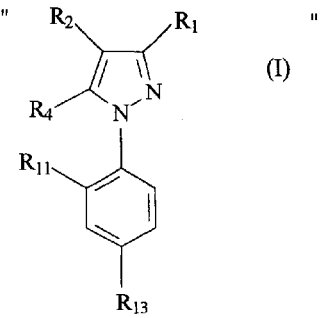  "

to read  --  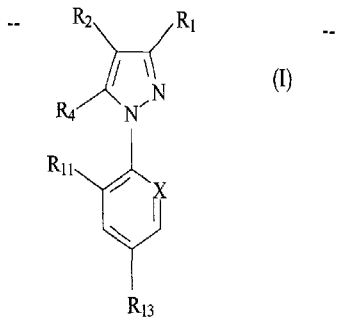  --

Signed and Sealed this

Seventeenth Day of August, 2004

JON W. DUDAS
*Acting Director of the United States Patent and Trademark Office*